United States Patent [19]

Webinger

[11] 4,163,518

[45] Aug. 7, 1979

[54] AIR FRESHENER CARTON

[75] Inventor: George P. Webinger, Minneapolis, Minn.

[73] Assignee: Champion International Corporation, Stamford, Conn.

[21] Appl. No.: 914,008

[22] Filed: Jun. 9, 1978

[51] Int. Cl.² .............................. A61L 9/04; B65D 5/36
[52] U.S. Cl. ............................................ 229/8; 239/60; 229/4.5
[58] Field of Search .............................. 229/8, 4.5, 37; 239/51.5, 54, 55, 57, 60

[56] References Cited

U.S. PATENT DOCUMENTS

| | | | |
|---|---|---|---|
| 2,004,818 | 6/1935 | Luckett | 229/4.5 X |
| 2,050,894 | 8/1936 | Paige | 229/8 X |
| 2,067,998 | 1/1937 | Williamson | 229/8 X |
| 2,344,359 | 3/1944 | Lehmann | 229/4.5 X |
| 3,021,045 | 2/1962 | Morris | 229/8 X |
| 3,302,845 | 2/1967 | Gould | 229/8 X |
| 3,610,514 | 10/1971 | Samsing | 229/8 X |
| 3,821,423 | 6/1974 | Jamin | 229/8 X |
| 3,851,813 | 12/1974 | Smith | 229/4.5 X |
| 3,877,632 | 4/1975 | Steel | 229/8 |
| 3,910,495 | 10/1975 | Cummings et al. | 239/60 X |

FOREIGN PATENT DOCUMENTS

| | | | |
|---|---|---|---|
| 942748 | 11/1963 | United Kingdom | 229/8 |
| 1033661 | 6/1966 | United Kingdom | 229/8 |

Primary Examiner—Davis T. Moorhead
Attorney, Agent, or Firm—Evelyn M. Sommer

[57] ABSTRACT

A one-piece carton for receiving an insert of air freshener material or the like includes a front panel and flanking back panels having a continuous curved lower edge. The common side edges of the front panel and back panels are defined by straight fold lines which converge as they extend away from the lower edge. Each of the panels includes a top flap which is shorter than the upper edge of the panel from which it extends. The free edges of the back panels are secured in overlapping relationship by an adhesive strip on one of the panels. The top flaps are folded inwardly and secured in overlapping relationship to form a rectangular top closure. An insert of air freshener material may be loaded into the carton through the generally circular, open bottom.

12 Claims, 6 Drawing Figures

AIR FRESHENER CARTON

BACKGROUND OF THE INVENTION

The present invention relates to cartons and more particularly, to a generally tapered carton for receiving an insert of solid air freshener material.

Solid air fresheners are often sold in sealed outer containers having one or more openings in the container walls to permit room air to circulate past the air freshener material. The openings are normally covered by a panel of release paper until a consumer is ready to use the air freshener material. The panel is then stripped away to expose the openings and thus the surface of the solid air freshener to room air.

Air freshener containers of molded plastic are known. Such molded plastic containers normally include a shell and a separate front piece which is affixed to the shell only after the solid air freshener has been loaded into place. While molded pastic shells may have an esthetically pleasing appearance, which is important in marketing the product, the costs of manufacturing and using such molded plastic containers are higher than might be desired. The shell and front piece must be molded in separate operations and stored in unassembled form until the solid air freshener is loaded into place. Then, the front piece must be glued or otherwise secured to the shell to close the carton.

The extra time required to manufacture and assemble containers from the two separate molded plastic pieces can be translated into terms of increased manufacturing costs. Moreover, since the plastic shells must be shipped and stored in their molded, unassembled form, transportation and/or storage costs may be incurred by a manufacturer who must then either absorb those costs or pass them on to the consumer in the form of higher product prices.

SUMMARY OF THE INVENTION

The present invention is a one-piece carton which may be made from a low cost, foldable material such as paperboard and which may be shipped and stored in a flattened or collapsed condition until ready to be loaded with an insert of solid air freshener material or the like.

A blank for making such a carton includes a front panel having a convex lower edge, first and second side edges defined by straight fold lines which converge as the extend away from the lower edge and an upper edge having a central segment defined by a straight fold line and first and second side segments, each of which extend away from one end of the central segment to the adjacent side edge of the front panel. The blank further includes first and second back panels, each of which extends from a side edge of the front panel to a free edge. Each of the back panels has a curved lower edge which is a continuation of the lower edge of the front panel and an upper edge which includes a segment defined by a straight fold line extending between the free edge of the back panel and a point spaced from the adjacent side edge of the front panel. A generally rectangular top front flap extends upwardly from the central segment of the front panel. First and second generally rectangular top back flaps extend upwardly from the straight segments at the upper edges of each of the back panels.

A carton is formed from this blank by fastening the free edges of the back panels together in overlapping relationship. The top back flaps are folded forward and the top front flap is folded backward and bonded to the top back flaps in overlapping relationship by means of a layer of adhesive on one surface of the top front flap. The carton is generally tapered or funnel shaped, having a generally circular opening at the lower edge for receiving an insert of air freshener material or the like.

DESCRIPTION OF THE DRAWINGS

While the specification concludes with claims particularly pointing out and distinctly claiming that which is regarded as the present invention, further details of preferred embodiments of the invention may be more readily ascertained from the following detailed description when read in conjunction with the accompanying drawings wherein:

DETAILED DESCRIPTION OF THE PREFERRED EMBODIMENTS

Figure 1:
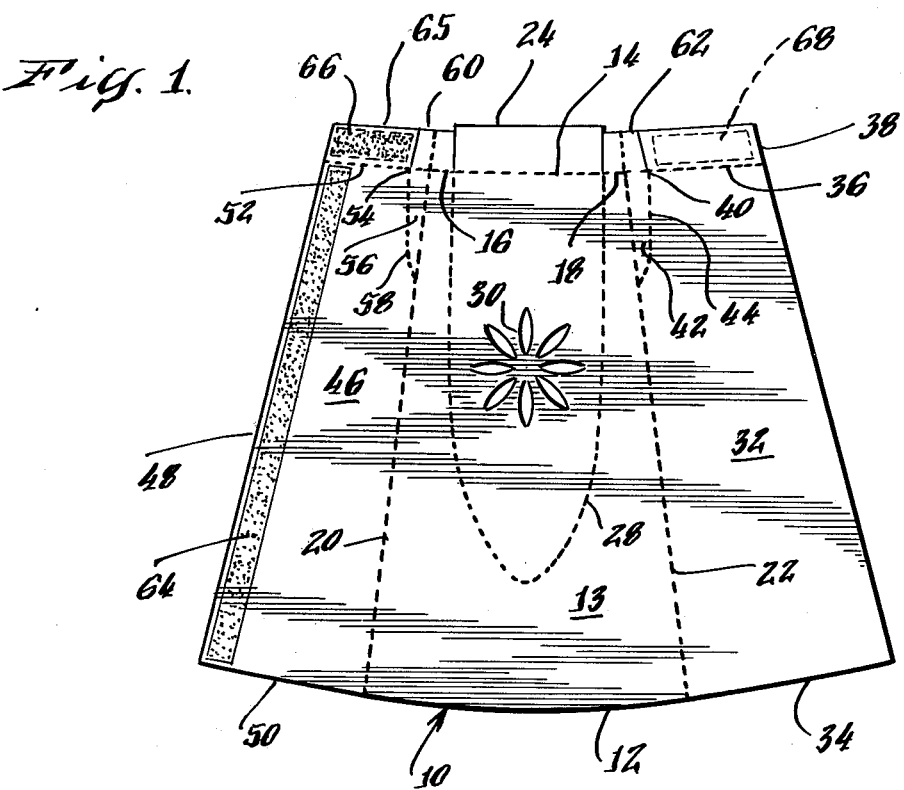
FIG. 1 is a plan view of a blank made in accordance with the present invention, which blank may be formed into a preferred carton embodiment.

Referring now to the drawings and particularly to FIG. 1, a blank for making a preferred type of carton includes a generally trapezoidal front panel 10 having a curved lower edge 12 and a spaced upper edge having a central segment 14 defined by a straight fold line and side segments 16 and 18, also defined by straight fold lines extending from opposite ends of the segment 14 to adjacent side edges of the front panel. The side edges of the front panel are defined by straight fold lines 20 and 22 which converge toward one another as they extend away from the lower edge 12 of the front panel. While segments 16 and 18 extending between opposite ends of the central segment 14 and the adjacent side edges of the front panel 10 are straight, they are not colinear with straight segment 14 but instead are sloped slightly upwardly.

A generally rectangular top front flap 24 extends upwardly from the fold line 14. In one embodiment of the invention, a generally parabolic fold line 28 within front panel 10 has its end points at opposite ends of the fold line 14. The parabolic fold line 28 divides the front panel 10 into an upper, essentially planar panel 11 which may have decoratively configured openings 30 and a roughly U-shaped lower panel 13 which will have a more cylindrical, rounded configuration in the finished carton.

The blank further includes a first back panel 32 connected to the front panel 10 along the fold line 22. The lower edge 34 of the first back panel 32 is a continuation of the lower edge 12 of the front panel 10. The first back panel 32 includes a straight segment 36 at its upper edge from which a generally rectangular top back flap 38 extends. The straight segment 36 extends from the free edge of back panel 32 to a point 40 spaced from the side edge 22. An expansion panel 42 is incorporated into the back panel 32. Expansion panel 42, the function of which will be described later, has a first edge defined by the fold line 22 and a second, curved edge 44 defined by a fold line which extends between one point on the side edge 22 and one end of the straight segment 36 at the upper edge of back panel 32.

The blank further includes a second back panel 46 having one edge defined by the fold line 20 and a free edge 48. The lower edge 50 of back panel 46 is a curved continuation of the lower edge of front panel 10. The upper edge of back panel 46 includes a straight segment 52 defined by a fold line extending from the free edge 48 to a point 54 spaced from the fold line 20. Back panel 46 also includes an expansion panel 56 having a first edge defined by the fold line 20 and a second curved edge defined by a fold line 58 extending from a point on fold line 20 to point 54 at the upper edge of the back panel 46. A rectangular top flap 65 extends upwardly from the straight segment 52.

In a preferred embodiment of the invention, a first top side flap 60 is centered on fold line 20 and extends between point 54 and the left edge of flap 24. A second top side flap 62 is centered on fold line 22 and extends between point 40 and the right edge of flap 24. The top side flaps 60 and 62 are bisected by continuations of the fold lines 20 and 22, respectively.

Predetermined areas of the blank are covered with a layer of pressure or heat sensitive adhesive. More specifically, an adhesive strip 64 extends substantially from the lower edge 50 of the back panel 46 to the straight segment 52. Approximately the left half of both surfaces of top flap 65 are coated with adhesive spots 66. The under surface of top flap 38 is similarly provided with an adhesive strip, indicated by dotted lines 68. A conventional wet glue can also be applied after erection of the carton on the mandrel.

Typically, the blank of FIG. 1 is automatically formed into a tapered carton by means of a machine including a mandrel about which the blank might be wrapped. The following description contains no reference to such a machine since the blank may be readily formed into a tapered carton by means of a simple series of automatic or manual folding operations.

The first step in forming a carton from the blank of FIG. 1 is to fold the first back panel 32 about the fold line 22 to the left or in the direction indicated by the arrow 70 to bring the back panel into contact with the front panel 10.

Figure 2:
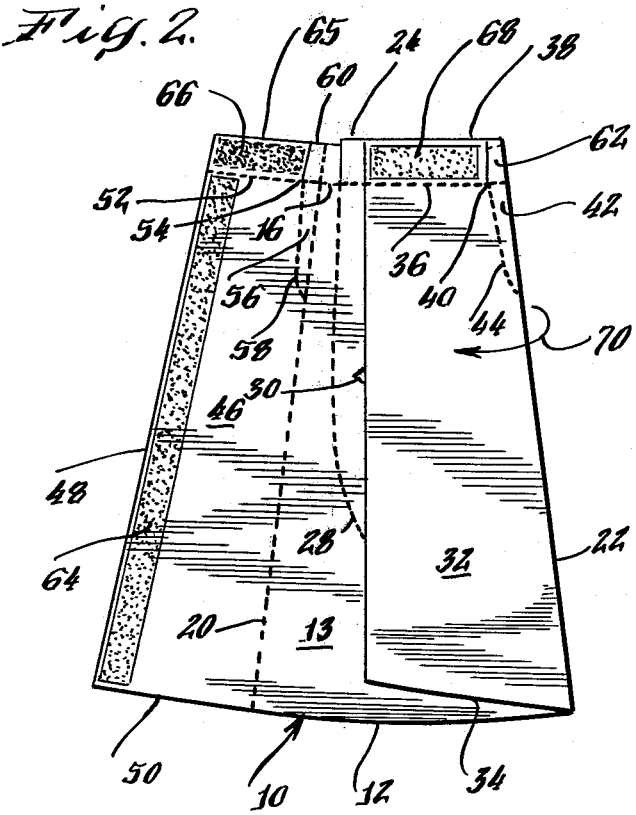
FIG. 2 is a plan view showing one step during manufacture of a carton from the blank of FIG. 1.
Figure 3:
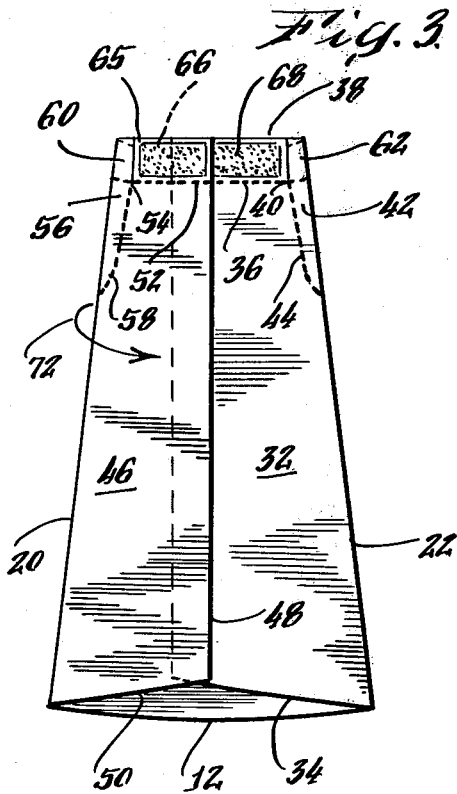
FIG. 3 is a plan view showing a subsequent step during manufacture of the carton.

Referring to FIG. 3, the second step in forming the blank is to fold the second back panel 46 to the right about fold line 20 to bring the adhesive coated area 64 into engagement with the surface of back panel 32 adjacent the free edge of that back panel. As can be seen in FIGS. 1 and 2, the free edge of back panel 32 extends well beyond the middle of the front panel 10 so that the back panels 32 and 46 overlap when folded into the position shown in FIG. 3. Back flaps 38 and 65 are secured to form an effective single back flap by the adhesive coated area 66 on back flap 65.

Figure 4:
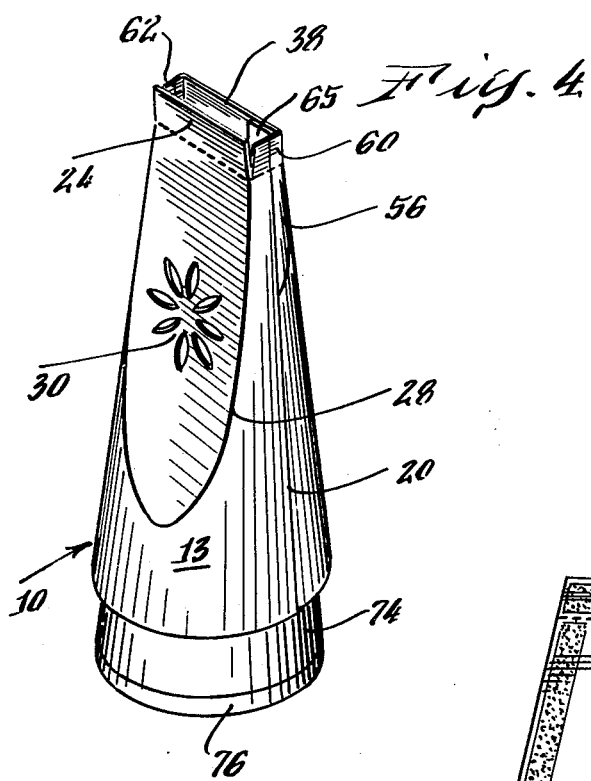
FIG. 4 is a perspective view of a partially completed carton made from the blank of FIG. 1.

The carton is, at this point, still in a completely flattened or collapsed condition. It can therefore be shipped and stored relatively easily. When the carton is to be used, it is formed into a tapered carton having a round bottom opening by pushing together the material at the fold lines 20 and 22. The expanded carton which results is shown in FIG. 4 along with an insert 74 of solid air freshener material seated on a base member 76 having a circumferential configuration which matches the configuration of the carton at its lower edge.

The top of the carton is shown as being open at this point. In actual practice, the carton top would be closed before the insert 74 is loaded into place. The carton top is closed by first folding the side flaps 62 and 60 inwardly. The back flap comprising the overlapped back flaps 38 and 65 is then folded forward to expose the adhesive coated areas 66 and 68. Finally, the front flap 24 is folded backward and into contact with the adhesive coated areas 66 and 68. As can be seen in FIG. 4, the expansion panels 56 and 42 allow the open top end of the container to assume a more rectangular configuration, making it easier to provide a rectangular top closure with a neat appearance. The base 76 for the air freshener material would, of course, be glued or otherwise secured in place in the finished carton.

The air freshener material can, as previously noted, be loaded into the carton through the generally circular, open bottom or in the alternative the air freshener material in a fluid viscous form can be introduced through a fill hole after the circular base has been sealed into the bottom of the assembled carton.

Figure 5:
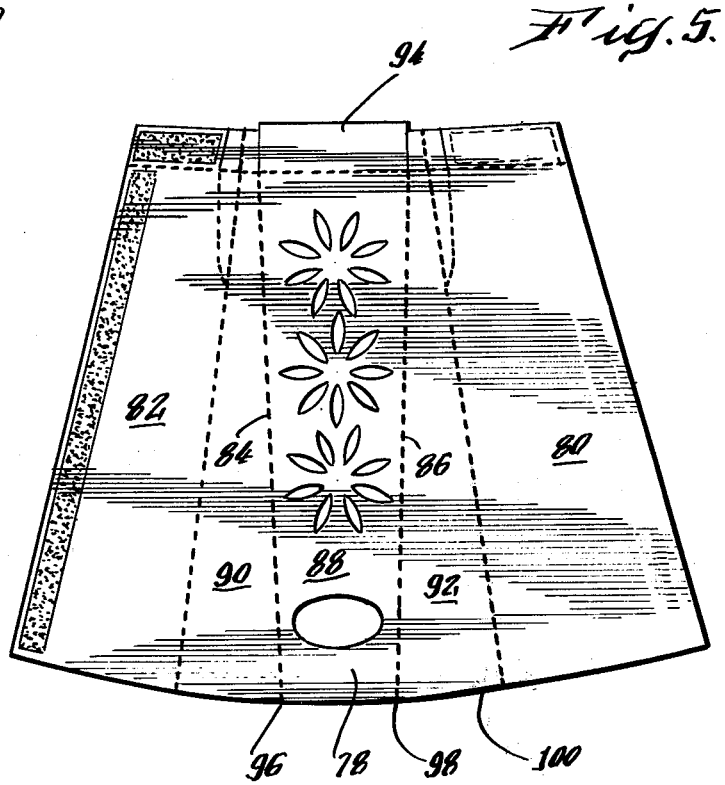
FIG. 5 is a plan view of an alternate embodiment of a blank made in accordance with the present invention.

The carton described with reference to the foregoing figures includes the generally parabolic fold line 28 which permits the upper portion of the front panel 10 to remain relatively flat in the formed carton. FIG. 5 depicts a blank which may be used to form an alternate type of carton. The blank includes a front panel 78 and first and second back panels 80 and 82, respectively. The configuration of each of the back panels 80 and 82 is identical to the configuration of corresponding panels of the blank described with reference to FIG. 1. The only difference between the blanks of FIG. 1 and FIG. 5 is in the front panel 78. Front panel 78 does not have a parabolic fold line but instead has additional interior fold lines 84 and 86 which divide the front panel 78 into a central, roughly rectangular panel 88 flanked by roughly triangular panels 90 and 92. The fold lines 84 and 86 converge slightly as they extend from opposite ends of a top front flap 94 to spaced points 96 and 98 on a lower edge 100 of the front panel 78. In a preferred embodiment, the segment of the panel 88 connecting the points 96 and 98 is a straight line while the remainder of the lower edge of the blank is a continuous curve.

Figure 6:
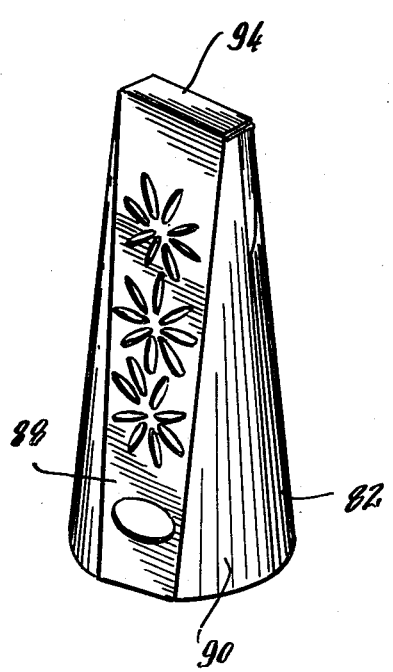
FIG. 6 is a perspective view of a completed carton made from the blank of FIG. 5.

The blank shown in FIG. 5 is folded in the manner described with reference to FIGS. 2 through 4 to provide a tapered carton having a generally circular bottom opening. Actually, as can be seen in FIG. 6, the bottom of the carton is not completely circular as it includes a flat edge at the lower edge of the central front panel 88.

While there have been described what are considered to be preferred embodiments of the present invention, variations and modifications therein will occur to those skilled in the art. For example, while the preferred embodiments of the invention employ top side flaps to more completely seal and lend rigidity to the top closure of the carton, such side flaps may be omitted if desired. Moreover, the front panel of the carton may be divided by interior fold lines of types other than those described herein for aesthetic purposes. Therefore, it is intended that the appended claims should be construed to include all such variations and modifications as fall within the true spirit and scope of the invention.

What is claimed as new is:

1. A carton having a bottom opening for receiving an insert comprising:

a front panel having a convex lower edge, first and second side edges defined by straight fold lines which converge as they extend away from said lower edge, and an upper edge having a central segment defined by a straight fold line and first and second side segments, each extending from one end of said central segment to the adjacent side edge of said front panel;

first and second back panels, each extending from a side edge of said front panel to a free edge and having a curved lower edge which is a continuation of the lower edge of said front panel and an upper edge including a segment defined by a straight fold line extending between the free edge of the panel and a point spaced from the adjacent side edge of said front panel, said first and second back panels being secured to one another in overlapping relationship; and a top closure including a front panel extending from the central segment of said front panel and a back flap comprising overlapping flaps extending from the straight segments at the upper edges of said first and second back panels, said front flap and said back flap being secured to one another in overlapping relationship.

2. A carton as defined in claim 1 further including first and second top side flaps centered on the fold lines defining the side edges of said front panel, each of said top side flaps extending from an end of the central segment of said front panel to an adjacent end of the straight segment of the adjacent back panel.

3. A carton as defined in claim 2 wherein each of said top side flaps is bisected by a continuation of the fold line defining the adjacent side edge of said front panel.

4. A carton as defined in either of claims 1 and 3 further including first and second expansion panels incorporated into said first and second back panels, respectively, each having a first edge defined by a side edge of said front panel and a second edge defined by a curved fold line extending between said side edge and the adjacent end of the straight segment at the upper edge of said back panels.

5. A carton as defined in claim 4 wherein said front panel further includes first and second interior fold lines extending from opposite ends of the central segment at the upper edge to spaced points on the curved lower edge thereof, said fold lines converging as they approach the lower edge.

6. A carton as defined in claim 4 wherein said front panel further includes a continuous, curved fold line extending across said front panel and terminating at opposite ends of said central segment, said continuous, curved fold line defining a planar panel section within said front panel.

7. A blank for a carton having a bottom opening for receiving an insert when erected, said blank comprising:

a front panel having a convex lower edge, first and second side edges defined by straight fold lines which converge as they extend away from said lower edge; and an upper edge having a central segment defined by a straight fold line and first and second side segments, each extending from one end of said central segment to the adjacent side edge of said front panel;

first and second back panels, each extending from a side edge of said front panel to a free edge and having a curved lower edge which is a continuation of the lower edge of said front panel and an upper edge including a segment defined by a straight fold line extending between the free edge of the panel and a point spaced from the adjacent side edge of said front panel;

a generally rectangular top front flap extending upwardly from the central segment of said front panel; and first and second generally rectangular top back flaps extending upwardly from the straight segments at the upper edges of each of said back panels.

8. A blank as defined in claim 7 further including first and second top side flaps, each of said flaps being centered on a side edge of said front panel and having a first side edge adjacent one end of said central segment and a second side edge adjacent one end of a straight segment at the upper edge of a back panel.

9. A blank as defined in claim 8 wherein each of said top side flaps is bisected by a continuation of the fold line defining the adjacent side edge of said front panel.

10. A blank as defined in either of claims 7 and 9 further including first and second expansion panels incorporated into said first and second back panels, respectively, each of said expansion panels having a first edge defined by a side edge of said front panel and a second edge defined by a curved fold line extending between said side edge and the adjacent end of the straight segment at the upper edge of the back panel.

11. A blank as defined in claim 10 wherein said front panel further includes first and second interior fold lines extending from opposite edges of the central segment to spaced points on the curved lower edge, said interior fold lines dividing said front panel into a central section and flanking, generally triangular sections.

12. A blank as defined in claim 10 wherein said front panel is divided into an upper section and a lower section by a generally parabolic fold line having its end points at opposite ends of the central segment.

* * * * *

UNITED STATES PATENT AND TRADEMARK OFFICE
CERTIFICATE OF CORRECTION

PATENT NO. : 4,163,518

DATED : August 7, 1979

INVENTOR(S) : George Webinger

It is certified that error appears in the above-identified patent and that said Letters Patent are hereby corrected as shown below:

In Column 1, line 20, delete the word "pastic" and insert in lieu thereof -- plastic --.

In Column 1, line 48, delete the word "the" (first word of line 48) and insert in lieu thereof -- they --.

In Column 5, line 20, delete the word "panel" (appears before words "extending from") and insert in lieu thereof -- flap --.

Signed and Sealed this

Sixth Day of May 1980

[SEAL]

Attest:

SIDNEY A. DIAMOND

*Attesting Officer*  *Commissioner of Patents and Trademarks*